United States Patent [19]

Hahn et al.

[11] Patent Number: 4,655,220

[45] Date of Patent: Apr. 7, 1987

[54] APPARATUS FOR CONTACTLESS FRAGMENTATION OF CONCREMENTS IN VIVO

[75] Inventors: Alfred Hahn; George Vogel, both of Erlangen, Fed. Rep. of Germany

[73] Assignee: Siekens Aktiengesellschaft, Berlin and Munich, Fed. Rep. of Germany

[21] Appl. No.: 694,578

[22] Filed: Jan. 24, 1985

[30] Foreign Application Priority Data

Apr. 27, 1984 [DE] Fed. Rep. of Germany ....... 8413031

[51] Int. Cl.[4] .............................................. A61B 17/22

[52] U.S. Cl. ..................................... 128/328; 367/140

[58] Field of Search ..................... 128/24 A, 328, 660; 367/140, 142; 310/11

[56] References Cited

FOREIGN PATENT DOCUMENTS 3312014 10/1984 Fed. Rep. of Germany ...... 128/328

2140693 12/1984 United Kingdom ................ 128/328

*Primary Examiner*—Clifford D. Crowder

*Attorney, Agent, or Firm*—Mark H. Jay

[57] ABSTRACT

The invention relates to an apparatus for the contactless fragmentation of a concrement present in the body of a living being. A shock wave generator is aimed at a target region in the body and includes a coil having the form of a spherical segment. In front of the coil is arranged a mating radiator element, which closes off a liquid filled space and generates therein a shock wave focused on the centers of curvature of the coil and element upon brief connection of the coil to a high voltage. The concrement to be fragmented is positioned to lie at these centers of curvature.

2 Claims, 1 Drawing Figure

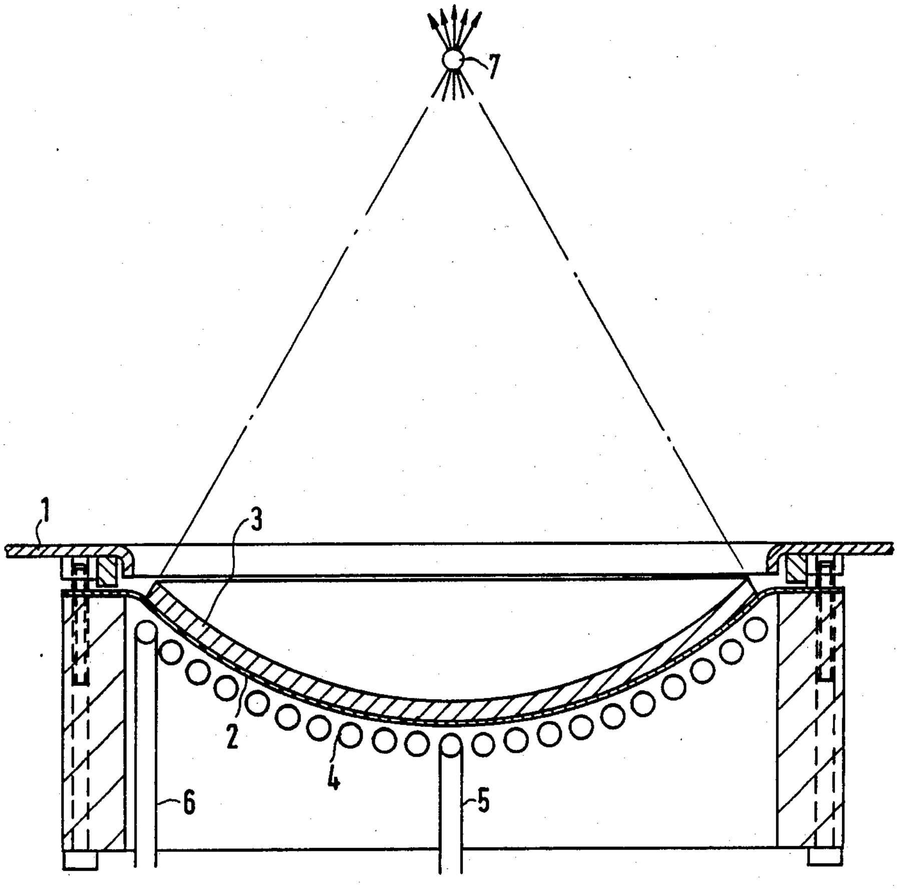
7
1
3
2
4
6
5

APPARATUS FOR CONTACTLESS FRAGMENTATION OF CONCREMENTS IN VIVO

BACKGROUND OF THE INVENTION

The invention relates to an apparatus for the contactless fragmentation of concrements present in the body of a living being, with a shock wave generator which is aimed at a target region in the body and which includes a planar coil. A radiator element lies in front of the coil and closes off a liquid-filled space, and generates a shock wave therein upon brief connection of the coil to a high voltage.

The coil may be formed, according to the journal "Akustische Beihefte", 1962, Volume 1, pages 185 to 202, as a flat coil and may be located at one end of a fully closed, liquid-filled shock wave tube. At the other end of the shock wave tube, a flexible bag may be provided, by which the shock wave tube is applied to the surface of the body to be treated. Since in this case the generated shock wave is planar and must be focused on the concrement to be fragmented, an adjustable acoustic lens for focusing the shock wave may be provided in the shock wave tube. The structural design of such an apparatus requires a relatively great overall length of about one half meter.

It is one object of the invention to simplify apparatus of the initially mentioned kind, particularly by eliminating the acoustic focusing lens.

It is another object to generally improve on the prior art.

SUMMARY OF THE INVENTION

According to the invention, the coil and the radiator element have the form of a spherical segment i.e. the form of a portion of a hollow sphere. With this design the shock wave is focused on the centers of curvature of the coil and element, where the concrement to be fragmented must be positioned. The radiator element from which the shock wave emanates may form the portion of the wall of a liquid-filled tub in which the body lies for fragmentation of the concrement.

BRIEF DESCRIPTION OF THE DRAWINGS

An exemplary and non-limiting preferred embodiment of the invention is illustrated in the single drawing.

DETAILED DESCRIPTION OF THE PREFERRED EMBODIMENTS

The drawing shows the lower portion of a treatment tub 1, in which a flexible membrane 2 is inserted. The membrane 2 carries a shell 3 which serves as a radiator element for the shock waves and is shaped as a spherical segment. The membrane 2 is fastened elastically in the treatment tub 1, as by screw connections. Behind the membrane 2 is located a coil 4 which, like the membrane 2 and shell 3, has the form of a section of a hollow sphere. The coil 4 extends in a spiral from the apex of the shell 3 to its edge. Accordingly, the connections 5, 6 to coil 4 are provided respectively at the center and edge of coil 4.

For fragmentation of a concrement 7 in the body of a living being (not shown), this body is so positioned in the water-filled treatment tub 1 that the concrement 7 lies at the centers of curvature of the coil 4 and the shell 3 (which latter may be rigid). Then, a high voltage (e.g. 20 kV) is generated, as by a capacitor-resistor circuit. This high voltage is briefly applied to coil 4, whereupon at least a part of the energy stored in the capacitor discharges abruptly into coil 4. With that, a magnetic field is built up very rapidly, which induces in the shell 3, consisting e.g. of copper, a current which is inverse to the current in coil 4 and produces an opposing magnetic field. By the force of the opposing field the shell 3 is knocked away from coil 4, the membrane 2 yielding resiliently. This knocking away of the shell 3 generates a shock wave, which is focused on the center of curvature of the shell 3 and hence on the concrement 7 positioned there. This fragments the concrement 7.

Those skilled in the art will understand that changes can be made in the preferred embodiments here described, and that these embodiments can be used for other purposes. Such changes and uses are within the scope of the invention, which is limited only by the claims which follow.

What is claimed is:

1. Shock wave generator apparatus for fragmenting concretions in vivo, comprising:

a radiator element bounding a liquid-filled volume and shaped as a spherical segment which is smaller than a hemisphere and which faces concave forward into said volume, the volume being large enough to receive a concretion to be destroyed; and a coil located behind the radiator element and shaped as a spherical segment which is smaller than a hemisphere and which faces concave forward to conform with the radiator element, the coil and radiator element being so coupled together that when the coil is briefly energized by a high voltage, the radiator element generates a shock wave in said liquid.

2. The apparatus of claim 1, wherein the radiator element and coil are positioned such as to have a common focus which is at their respective centers of curvature.

* * * * *